US008229186B2

(12) United States Patent
Milstein et al.

(10) Patent No.: US 8,229,186 B2
(45) Date of Patent: Jul. 24, 2012

(54) VESSEL CENTERLINE DETERMINATION

(75) Inventors: Ido Milstein, Tel-Aviv (IL); Shmuel Akerman, Binyamina (IL); Gad Miller, Paris (FR); Laurent Cohen, Neuilly sur Seine (FR)

(73) Assignee: Algotec Systems Ltd., RaAnana (IL)

( * ) Notice: Subject to any disclaimer, the term of this patent is extended or adjusted under 35 U.S.C. 154(b) by 1160 days.

(21) Appl. No.: 10/597,226

(22) PCT Filed: Dec. 26, 2004

(86) PCT No.: PCT/IL2004/001169
§ 371 (c)(1),
(2), (4) Date: Jan. 22, 2008

(87) PCT Pub. No.: WO2005/069223
PCT Pub. Date: Jul. 28, 2005

(65) Prior Publication Data
US 2008/0132774 A1   Jun. 5, 2008

Related U.S. Application Data

(60) Provisional application No. 60/536,661, filed on Jan. 15, 2004.

(51) Int. Cl.
G06K 9/20 (2006.01)
G06K 9/34 (2006.01)
(52) U.S. Cl. ........ 382/128; 382/130; 382/131; 382/132; 382/171; 382/173; 382/276
(58) Field of Classification Search .................. 382/128, 382/130, 131, 132, 171, 173, 276
See application file for complete search history.

(56) References Cited

U.S. PATENT DOCUMENTS

| 5,394,325 A | 2/1995 | Schneider, Jr. |
| 5,752,217 A | 5/1998 | Ishizaki et al. |
| 5,878,368 A | 3/1999 | DeGraaf |
| 6,038,509 A | 3/2000 | Poppen et al. |
| 6,324,478 B1 | 11/2001 | Popovici et al. |
| 6,418,373 B1 | 7/2002 | Omi et al. |
| 6,470,266 B1 | 10/2002 | Ito et al. |
| 6,496,188 B1 | 12/2002 | Deschamps et al. |
| 6,604,005 B1 | 8/2003 | Dorst et al. |

(Continued)

FOREIGN PATENT DOCUMENTS
WO    WO 2004/086310    10/2004
(Continued)

OTHER PUBLICATIONS

International Preliminary Report on Patentability Dated Jul. 27, 2006 From the International Bureau of WIPO Re.: Application No. PCT/IL2004/001168.

(Continued)

Primary Examiner — David A Vanore
Assistant Examiner — Nicole Ippolito

(57) ABSTRACT

A method of centerline determination for a tubular tissue in a medical image data set defined in a data space, comprising receiving at least one start point and one end point inside a tubular tissue volume; automatically determining a path between said points that remains inside said volume; automatically segmenting said tubular tissue using said path; and automatically determining a centerline for said tubular tissue from said segmentation, wherein said receiving, said determining a path and said segmenting, said determining a centerline are all performed on a same data space of said medical image data set.

69 Claims, 5 Drawing Sheets

U.S. PATENT DOCUMENTS

| | | |
|---|---|---|
| 6,687,615 B1 | 2/2004 | Krull et al. |
| 2002/0100009 A1* | 7/2002 | Xing et al. ................. 716/12 |
| 2002/0136437 A1* | 9/2002 | Gerard et al. ............... 382/128 |
| 2003/0031351 A1* | 2/2003 | Yim ............................. 382/130 |
| 2005/0110791 A1* | 5/2005 | Krishnamoorthy et al. .. 345/419 |
| 2005/0152588 A1* | 7/2005 | Yoshida et al. .............. 382/128 |
| 2008/0091340 A1 | 4/2008 | Milstein et al. |

FOREIGN PATENT DOCUMENTS

| | | |
|---|---|---|
| WO | WO 2005/069223 | 7/2005 |
| WO | WO 2005/069228 | 7/2005 |

OTHER PUBLICATIONS

International Preliminary Report on Patentability Dated Jul. 27, 2009 From the International Bureau of WIPO Re.: Application No. PCT/IL2004/001169.

International Search Report and the Written Opinion Dated Nov. 9, 2005 From the International Searching Authority Re.: Application No. PCT/IL2004/001169.

International Search Report and the Written Opinion Dated May 10, 2005 From the International Searching Authority Re.: Application No. PCT/IL2004/001168.

Official Action Dated Nov. 9, 2009 From the US Patent and Trademark Office Re.: U.S. Appl. No. 10/597,221.

Response Dated May 4, 2010 to Official Action of Nov. 9, 2009 From the US Patent and Trademark Office Re.: U.S. Appl. No. 10/597,221.

Official Action Dated Jul. 12, 2010 From the US Patent and Trademark Office Re.: U.S. Appl. No. 10/597,221.

Communication Relating to the Results of the Partial international Search Dated Jun. 2, 2005 From the International Searching Authority Re.: Application No. PCT/IL2004/001169.

Cohen et al. "Global Minimum for Active Contour Models: A Minimal Path Approach", International Journal of Computer Vision, 24(1): 57-78, 1997.

Cormen et al. "Introduction to Algorithms", 2nd Edition, MIT Press, Chap.22: 540-549, 2001.

Deschamps et al. "Fast Extraction of Minimal Paths in 3D Images and Applications to Virtual Endoscopy", Medical Image Analysis, 5: 281-299, 2001.

Li et al. "Combining Front Propagation With Shape Knowledge for Accurate Curvilinear Modeling", Medical Image Computing and Computer-Assisted Intervention—MICCAI 2003, 2879: 66-74, 2003.

Livingstone et al. "Fast Marching and Fast Driving: Combining Off-Line Search and Reactive A.I.", 4th International Conference on Intelligent Games and Simulation (Game-On 2993), 4 P., 2003.

Maddah et al. "Efficient Center-Line Extraction for Quantification of Vessels in Confocal Microscopy Images", Medical Physics, 30(2): 204-211, 2003.

Melchior et al. "Consideration of Obstacle Danger Level in Path Planning Using A* and Fast-Marching Optimisation: Comparative Study", Signal Processing, 83(11): 2387-2396, 2003.

Sethian "A Fast Marching Level Set Method for Monotonically Advancing Fronts", Proc. Natl. Acad. Sci. USA, 93(4): 1591-1595, 1996.

Sethian "Evolution, Implementation, and Application of Level Set and Fast Marching Methods for Advancing Fronts", Journal of Computational Physics, 169(2): 503-555, 2001.

Sethian "Fast Marching Methods", SIAM Review, 41(2): 199-235, 1999.

Sethian "Level Set Methods and Fast Marching Methods. Evolving Interfaces in Computational Geometry, Fluid Mechanics, Computer Vision, and Materials Science", Cambridge University Press, P.1-33, 1999. http://math.berkeley.edu/sethian/Books/sethian_book.ps.

Wink et al. "3D MRA Coronary Axis Determination Using A Minimum Cost Path Approach", Magnetic Resonance in Medicine, 47(6): 1169-1175, 2002.

Response Dated Nov. 11, 2010 to Official Action of 12 Jul. 2010 From the US Patent and Trademark Office Re.: U.S. Appl. No. 10/597,221.

Official Action Dated Oct. 7, 2011 From the US Patent and Trademark Office Re. U.S. Appl. No. 10/597,226.

Communication Pursuant to Article 94(3) EPC Dated Jan. 5, 2012 From the European Patent Office Re. Application No. 04806699.7.

Communication Pursuant to Article 94(3) EPC Dated Jan. 5, 2012 From the European Patent Office Re. Application No. 04806700.3.

* cited by examiner

VESSEL CENTERLINE DETERMINATION

RELATED APPLICATIONS

The present application is a US National Phase of PCT Application No. PCT/IL2004/001169, filed on Dec. 26, 2004, which claims the benefit under 35 U.S.C. 119(e) of U.S. Provisional Application 60/536,661 filed Jan. 15, 2004, the disclosure of which is incorporated herein by reference.

This application is also related to a PCT application No. PCT/IL2004/001168 entitled "Targeted Marching", filed on Dec. 26, 2004 the disclosure of which is incorporated herein by reference.

FIELD OF THE INVENTION

The present invention relates to the processing of data sets, for example medical image data sets obtained from CT images.

BACKGROUND OF THE INVENTION

CT imaging systems can be used for checking blood vessels, especially for detecting narrowing (stenosis) in the blood vessels. FIG. 1 is a schematic illustration of a display showing two blood vessel views, a view 100 showing a blood vessel 102 and a view 122, a slice generally perpendicular to vessel 102, along a plane marked as 120. It should be noted that in most situations, vessel 102 will not lie uniformly in one plane. It is desirable to determine a centerline 108 of vessel 102, so that slices 122 can be made perpendicular thereto and allowing various views along and of the blood vessel. For example, the vessel may be checked for narrowing by providing a series of slices perpendicular to the blood vessel or the vessel may be spread out into a flat image, for inspecting its wall.

An exemplary current practice is to have a user mark multiple points (e.g., 16-32 points) along an estimated centerline 108 and then connect them with straight lines or use various algorithmic methods to obtain a more exact determination of the centerline.

It should be noted that centerline determination is generally not a trivial task. In many cases parts of the blood vessel are missing, have non-uniform CT numbers (Hounsfield numbers) and/or the edges of the blood vessels are not clear. Exemplary reasons for this are:

(a) Even if the blood vessel is imaged using a contrast material, this material may not be uniformly distributed along the blood vessel.

(b) Partial volume effects, especially near bones.

(c) Nearby tissue with similar absorption (e.g., cortical bone, marrow and kidney tissue). For example, a boundary 118 might not be visible next to a bone 116.

(d) Narrowing, splitting and/or other geometrical properties of vessels.

(e) Some vessels contain stents.

(f) Nearby vessels may appear to meet and merge and then diverge.

(g) Various effects may cause a vessel to appear to include loops.

(h) An incorrect centerline can cause the appearance of a narrowing while viewing the vessel.

(i) An unsmooth centerline can cause difficulty in viewing and/or understanding the entire blood vessel.

j) Occlusions.

PCT publication WO 2004/086310, the disclosure of which is incorporated herein by reference, describes a method of curvilinear modeling. In this publication, a minimum cost path is converted into a curvilinear model of a tubular organ, by resampling the data around the minimal cost path into a transformed data domain and then further processing in that domain.

SUMMARY OF THE INVENTION

An aspect of some embodiments of the invention relates to a method of centerline determination, in which a blood vessel volume is identified based on an inaccurate internal path and then a more accurate centerline is determined. In an exemplary embodiment of the invention, the more accurate centerline is determined by segmenting the data set using the inaccurate centerline. This method may be applied to other lumens in a body as well, in some embodiments of the invention.

In an exemplary embodiment of the invention, a medical image data set is provided with an associated data space, such as a three-dimensional spatial grid. Both the initial path and the segmentation are applied without deforming the space in which the data set is provided.

An aspect of some embodiments of the invention relates to a targeted marching algorithm based method, in which a cost function of a point depends both on a local cost and on an estimated cost to reach a target. In an exemplary application, a contour is expanded from one or more starting points to a target point, with a heap or other data structure being used to store points and their associated cost. Once the contour passes a point, it is marked "alive" and taken out of the heap. In an exemplary embodiment of the invention, the estimated cost to target for a current point is based on a function of the geometrical distance to target and the average cost (per unit length) to the current point. Optionally, this cost is normalized, for example to equate between different starting points.

Optionally, if an "alive" point is reached by the contour a second time with a lower cost than before, it may be reinserted into the heap for further consideration. In an exemplary embodiment of the invention, the cost function is, at least most of the time, an estimate from below the real cost.

In an exemplary embodiment of the invention, targeted marching is used for finding an initial possibly inaccurate centerline (which is actually an internal path which may tend to the center). Optionally, one or more of the following properties are desired in the method used for finding this internal path, and may be provided by some implementations of targeted marching:

(a) geometrically correct distance calculations, resulting from a greater consistency with underlying continuous data than provided by other methods (e.g., as data is sampled finer, the accuracy of measurement increases); in one example correct diagonal distance calculations are provided;

(b) providing a path within the volume of the blood vessel;

(c) ability to work with a relatively small number of starting points; and (d) focusing a search propagation to within the blood vessel volume.

In other embodiments of the invention, a different path finding algorithm is used.

In some embodiments of the invention, targeted marching is used to find a more exact center line, once the blood vessel volume is identified.

An aspect of some embodiments of the invention relates to a method of segmentation of a blood vessel or other body duct, for separating out the data points of a blood vessel from a complete data set, in which different sections along the blood vessels are segmented from the data set using different local histograms for blood vessel data values. Optionally, the histograms are averaged for nearby segments. In an exemplary embodiment of the invention, the averaging is achieved by registering each point not only in its own histogram but also in its two neighboring histograms (e.g., of neighboring portions).

An aspect of some embodiments of the invention relates to a segmentation method in which a curvature limitation is applied during point propagation. Optionally, this curvature limitation trades-off the possibility of missing part of the vessel with the ability to reduce non-uniform leakage and/or bridge gaps.

An aspect of some embodiments of the invention relates to cost functions which reduce escape of a search point (e.g., at the edge of a contour) from a volume of a blood vessel. In an exemplary embodiment of the invention, a path finding method in a blood vessel uses a cost function for a point based on a distribution of data values, to determine a probability of the point being inside or outside of the blood vessel and/or an estimation of curvature. In an exemplary embodiment of the invention, a cost function includes a factor of an angle limitation, reducing angular motion of the search point relative to a starting point. In an exemplary embodiment of the invention, a cost function includes a distance limitation based on an average distance in the cost metric found in nearby sections of the blood vessel. In an exemplary embodiment of the invention, a cost function includes limiting the propagation of points from a same source that propagate too far (e.g., based on a parameter value). In an exemplary embodiment of the invention, a cost function includes a limitation that prevents forward (along the blood vessel) propagation, which also tends to limit leakage. Optionally, the leakage is reduced such that fewer than 50% fewer than 20% or fewer than 10% of the points considered by the segmentation method are leakage points, for a typical execution, for example on 50% of images for which a centerline is sought.

In some embodiments of the invention, a point is prevented from escaping from the blood vessel. In an exemplary embodiment of the invention, preventing from straying reduces calculation costs as fewer points need to be considered. In other embodiments, the point is allowed to escape but prevented from straying too far from the blood vessel. In an exemplary embodiment of the invention, if the straying is sufficiently reduced, calculation costs can be kept lower and/or the effect of the escape on the quality of segmentation is reduced.

An aspect of some embodiments of the invention relates to propagation of parameterization in which the parameter values are propagated in a manner which is uniform, smooth and/or generally parallel to a starting line. In an exemplary embodiment of the invention, parameterization values are propagated in an imaging dataset. In an exemplary embodiment of the invention, the propagation is used to collect statistics about a centerline or path. Such statistics are optionally used to reduce leakage.

An aspect of some embodiments of the invention relates to a method of finding a centerline, in a manner which trades off curvature (of the centerline) and staying in a center. Optionally, the method is generally indifferent to variations in vessel diameter and/or gives good results for large diameter vessels.

An aspect of some embodiments of the invention relates to centerline and/or segmentation finding method which has a typically CPU usage of O(nlogn) and/or a typical memory usage of O(n), where n is the number of points actually found inside the blood vessel section of interest. In an exemplary embodiment of the invention, these limits are available due to restricting leakage outside the blood vessel. In some cases an additional fixed cost is added, for example o(N), where N is the number of points in the whole data set, for forming of a histogram. Alternatively, a statistical histogram may be created, for example using only the same number of points as expected in the blood vessel or using a fixed number of points (e.g., 1000).

There is thus provided in accordance with an exemplary embodiment of the invention, a method of centerline determination for a tubular tissue in a medical image data set defined in a data space, comprising:

receiving at least one start point and one end point inside a tubular tissue volume;

automatically determining a path between said points that remains inside said volume;

automatically segmenting said tubular tissue using said path; and automatically determining a centerline for said tubular tissue from said segmentation, wherein said receiving, said determining a path and said segmenting, said determining a centerline are all performed on a same data space of said medical image data set. Optionally, said tubular tissue comprises a body lumen.

In an exemplary embodiment of the invention, receiving comprises receiving at most 4 points from a human user. Optionally, receiving comprises receiving at most 2 points from a human user.

In an exemplary embodiment of the invention, automatically determining a path comprises determining using targeted marching which uses a cost function incorporating both path cost and estimated future path cost. Optionally, determining a path comprises propagating a sub-path from each of at least two of said received points until the sub-paths meet. Alternatively or additionally, determining a path comprises propagating a sub-path from one of said received points until it meets another of the received points. Alternatively or additionally, propagating a sub-path comprises selecting a point and selecting a neighbor of the selected point for further consideration responsive to said cost function.

In an exemplary embodiment of the invention, a path cost of a point is a function of a local cost of a point and a path cost of at least one neighbor of the point. Optionally, a local cost of a point is a function of a probability of the point being inside or outside of the tubular tissue. Alternatively or additionally, a path cost is determined by finding at least an approximate solution to an equation including at least one extreme-type function that returns an extreme value of its operands. Optionally, if a solution is not found, at least one of said extreme-type functions is replaced by a constant value. Optionally, said extreme-type function to replace is found by a min-max method.

In an exemplary embodiment of the invention, said equation includes an approximation of a gradient of the path cost.

In an exemplary embodiment of the invention, a path cost of a point is a function of a probability of the point being inside or outside of the tubular tissue.

In an exemplary embodiment of the invention, said probability is determined using a histogram of data point values. Optionally, the method comprises updating the histogram when a point is determined to be inside or outside of the tubular tissue. Alternatively or additionally, the method comprises updating the histogram when a point is selected. Optionally, said histogram is updated with a weight corresponding to a probability of the point being inside the tubular tissue.

In an exemplary embodiment of the invention, the method comprises generating a local histogram for a part of said vessel.

In an exemplary embodiment of the invention, the histogram comprises an outside histogram for point values that are outside the tubular tissue. Optionally, the outside histogram includes also points inside the tubular tissue.

In an exemplary embodiment of the invention, the histogram comprises an inside histogram for point values that are inside the tubular tissue.

In an exemplary embodiment of the invention, the method comprises selecting a target to be used in an estimating of said future cost. Optionally, said estimating is an underestimating. Alternatively or additionally, said estimating is based on an average cost per distance unit. Alternatively or additionally, said estimating is based on an Euclidian distance to said target. Alternatively or additionally, selecting a target comprises selecting from two or more possible targets. Optionally, selecting a target comprises projecting two vectors, one for each of two potential targets on a vector connecting a current point with a starting point of the current point and selecting a longer projection.

In an exemplary embodiment of the invention, selecting a target comprises selecting one of said received points.

In an exemplary embodiment of the invention, automatically determining a path comprises determining using fast marching. Alternatively or additionally, automatically determining a path comprises determining using the A* path finding method. Alternatively or additionally, automatically determining a path comprises determining using Dijkstra's minimal length path finding method.

In an exemplary embodiment of the invention, the method comprises correcting said determined path. Optionally, correcting said path comprising interconnecting path segments.

In an exemplary embodiment of the invention, said segmenting uses a marching method for segmentation.

In an exemplary embodiment of the invention, said segmenting uses a contour expansion method.

In an exemplary embodiment of the invention, said marching method assigns a value for each point in said tubular tissue.

In an exemplary embodiment of the invention, said marching method is a fast marching method.

In an exemplary embodiment of the invention, said segmenting comprises parametrizing points along said path. Optionally, the method comprises propagating said parameterization. Optionally, said propagated parameterization is used to prevent leakage of said segmentation. Alternatively or additionally, said parameterization is propagated substantially parallel to said path. Optionally, the method comprises propagating said parameterization to being substantially perpendicular to a path cost gradient associated with said propagation.

In an exemplary embodiment of the invention, the method comprises collecting propagation statistics for different parameterization values. Alternatively or additionally, the method comprises determining a direction of propagation from a propagation of parameterization values.

In an exemplary embodiment of the invention, the method comprises controlling a direction of propagation based on said parameterization.

In an exemplary embodiment of the invention, the method comprises limiting propagation of at least one parameterization value based on said statistics. Optionally, limiting comprises limiting propagation to relatively locally uniform volume for nearby parameterizations.

In an exemplary embodiment of the invention, said segmenting comprises partitioning said path into portions. Optionally, the method comprises defining boundary planes between said portions. Alternatively or additionally, said portions overlap by a relatively small amount. Alternatively or additionally, said portions are substantially straight lines.

In an exemplary embodiment of the invention, said partitioning is used to reduce leakage of said segmentation.

In an exemplary embodiment of the invention, said segmenting comprises propagating from said path. Optionally, said propagating is limited to be relatively perpendicular to said path. Alternatively or additionally, said propagating is limited to be relatively locally uniform in a radial direction. Alternatively or additionally, said propagating depends on a local curvature. Optionally, said local curvature is estimated by counting visited neighbors.

In an exemplary embodiment of the invention, said segmenting comprises segmenting using a histogram of data values to determine a probability of a point being inside the tubular tissue. Optionally, different parts along said path have different histograms. Optionally, said histograms are created to vary smoothly between said parts. Alternatively or additionally, a noise level in at least one of said histograms is reduced using a global histogram.

In an exemplary embodiment of the invention, the method comprises repeatedly updating said histograms during said segmenting.

In an exemplary embodiment of the invention, the method comprises cleaning the segmentation.

In an exemplary embodiment of the invention, determining a centerline comprises generating a distance map of said tubular tissue, of distances from an outer boundary of said tubular tissue, inwards. Optionally, generating a distance map comprises using morphological skeletonization on said segmentation. Alternatively or additionally, determining a distance map comprises using fast marching on said segmentation. Alternatively or additionally, determining a centerline comprises finding a path in said distance map. Optionally, finding a path for said centerline comprises targeted marching from at least one end of said segmentation. Optionally, said targeted marching for finding a path comprises taking a local curvature into account.

In an exemplary embodiment of the invention, said data set is three dimensional.

There is also provided in accordance with an exemplary embodiment of the invention, a method of segmenting an organ in a medical image data set, comprising:

dividing said data set into portions; and using a different probability histogram in each of at least two of said portions for determining if a point belongs in the segmentation. Optionally, the method comprises smoothing at least two histograms, for two neighboring portions. Optionally, said smoothing comprises registering a plurality of points in both of said neighboring histograms.

In an exemplary embodiment of the invention, the method comprises correcting said different histograms using a global histogram that encompasses at least two of said different histograms.

There is also provided in accordance with an exemplary embodiment of the invention, a method of segmenting an organ in a medical image data set, comprising:

defining a plurality of partially overlapping portions in said data set, which portions cover at least one object of interest;

separately segmenting each of said portions; and combining said segmentations to yield a single segmentation of said at least one object. Optionally, said portions are selected to divide a tubular organ into substantially straight sections.

There is also provided in accordance with an exemplary embodiment of the invention a method of segmenting an organ in a medical image data set, comprising:

propagating a segmentation in said data set; and applying a curvature limitation to said propagation. Optionally, applying a curvature limitation comprises counting visited neighbors.

There is also provided in accordance with an exemplary embodiment of the invention, a method of propagating parameterization in a medical image data set, comprising:

providing an initial parameterization in said data set along at least one line;

propagating a parameterization from said line, wherein said propagation is limited to being substantially parallel to said at least one line. Optionally, the method comprises propagating said parameterization to have a gradient which is substantially perpendicular to a gradient of a path cost associated with said propagation. Alternatively or additionally, the method comprises limiting an angle between (a) a spatial vector defined between a starting point of the parameterization along said line and ending at a current point of propagation of parameterization and (b) said path, to being close to perpendicular. Optionally, said limiting comprises reducing leakage of a segmentation by said limiting.

In an exemplary embodiment of the invention, said medical image data set is a three-dimensional data set.

There is also provided in accordance with an exemplary embodiment of the invention, a method of centerline finding in a distance map, comprising:

providing a distance map of an organ having a centerline;

determining a desired tradeoff between curvature and (a) local curvature of a path and (b) remaining near said centerline; and finding a path in said map while applying limitations of (a) local curvature of the path and (b) remaining near said centerline, wherein said finding a path comprises applying said tradeoff in a manner which is uniform at points along a path in organs having cross-sectional areas different by more than 50%. Optionally, said limitations are applied as part of a targeted marching method in which a path is found by propagation of wave front using a cost function which depends on both a local cost and an estimated cost to target. Optionally, said trade-off is applied to at least two points in a same organ. Alternatively or additionally, said trade-off is applied to two different organs in a same data set.

In an exemplary embodiment of the invention, applying said tradeoff comprises using a formula for trading off which includes an exponent and normalization of organ diameter.

In an exemplary embodiment of the invention, said tradeoff is uniform on different parts of a cross-section of said organ over a range of at least 50% of said cross-section, such that same movement has a similar effect on curvature.

There is also provided in accordance with an exemplary embodiment of the invention, a method of centerline determination for a body tubular tissue in a medical data set, comprising:

providing a data set including a tubular tissue having n points in a three-dimensional medical dataset; and finding a path in said data set in O(nlogn) time of scalar calculation steps. Optionally, said path is found using no more than O(n) memory units.

There is also provided in accordance with an exemplary embodiment of the invention, a method of centerline determination for a body tubular tissue in a medical data set, comprising:

providing a data set including a tubular tissue having n points in a three-dimensional medical dataset; and finding a path in said data set using no more than O(n) memory units.

BRIEF DESCRIPTION OF THE FIGURES

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which.

DETAILED DESCRIPTION OF EXEMPLARY EMBODIMENTS

Overview of Method Description and Method

Figure 5:
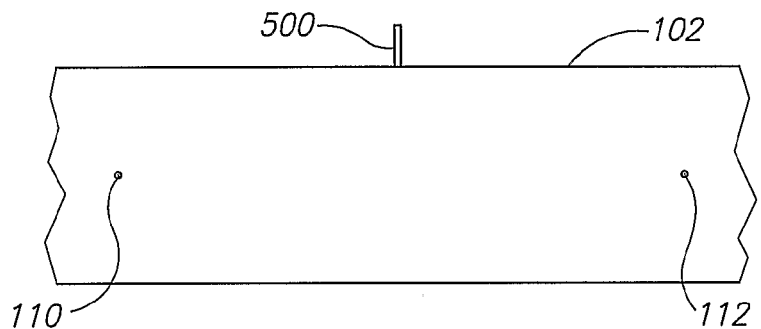
FIG. 5 illustrates an optional step of segmentation cleaning, in accordance with an exemplary embodiment of the invention.
Figure 6:
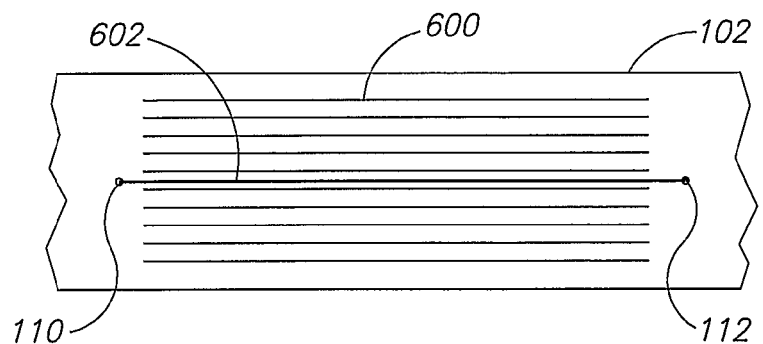
FIG. 6 illustrates a centerline determination, in accordance with an exemplary embodiment of the invention.
Figure 7:
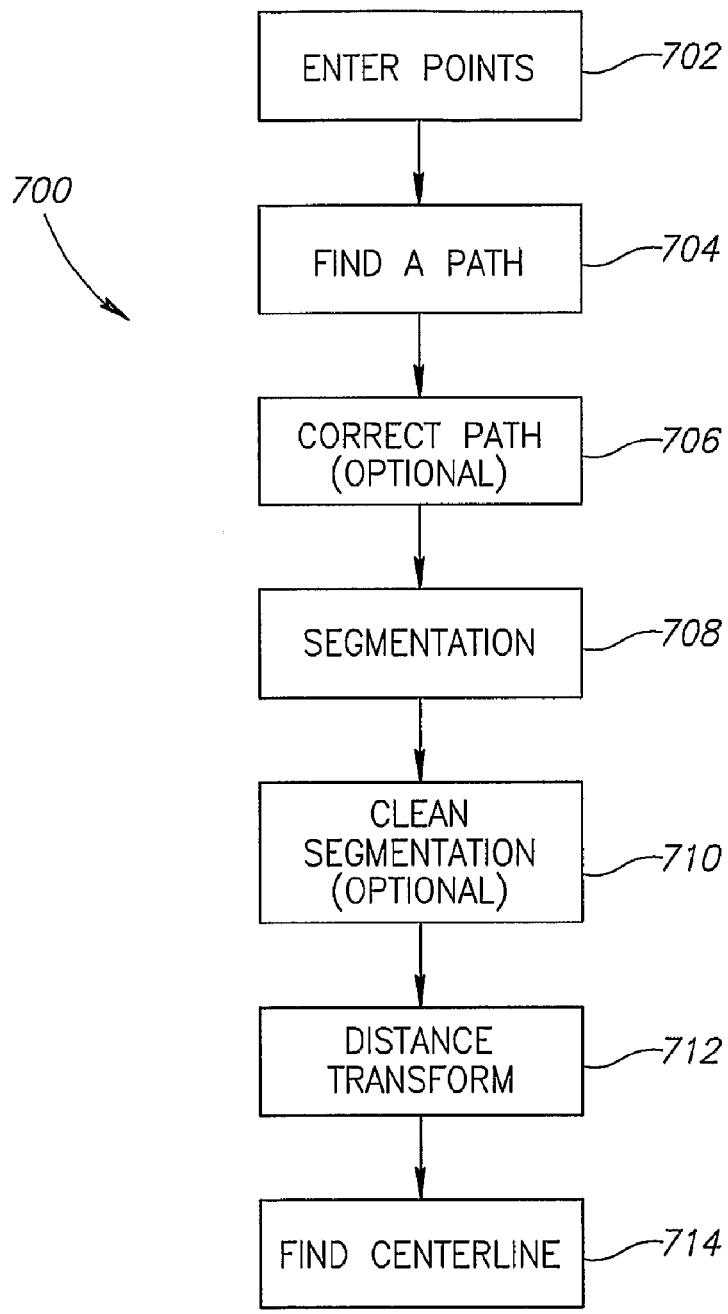
FIG. 7 is a flowchart of a method of centerline determination, in accordance with an exemplary embodiment of the invention.
Figure 8:
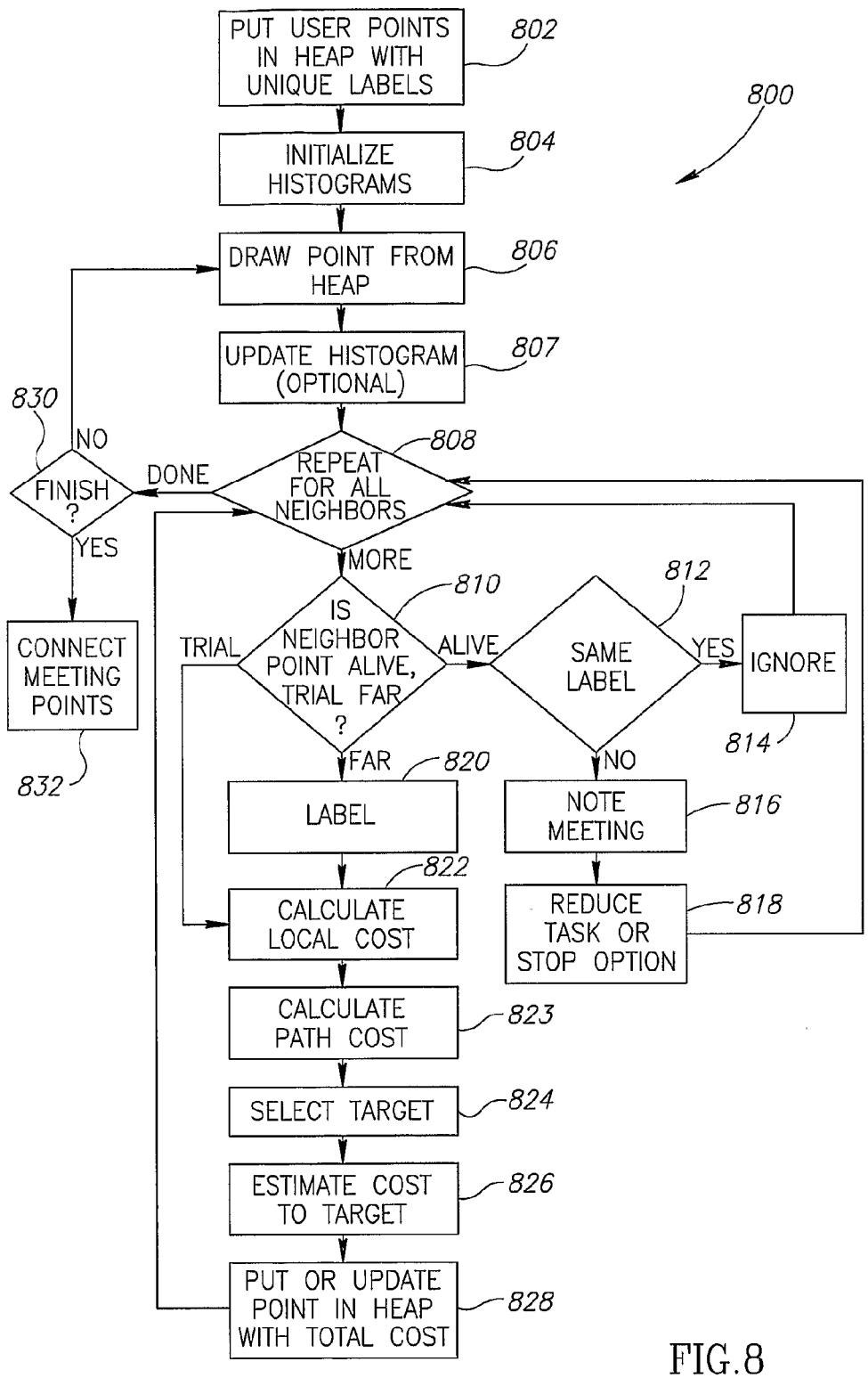
FIG. 8 is a flowchart of a method of finding an initial path in a blood vessel, in accordance with an exemplary embodiment of the invention.
Figure 9:
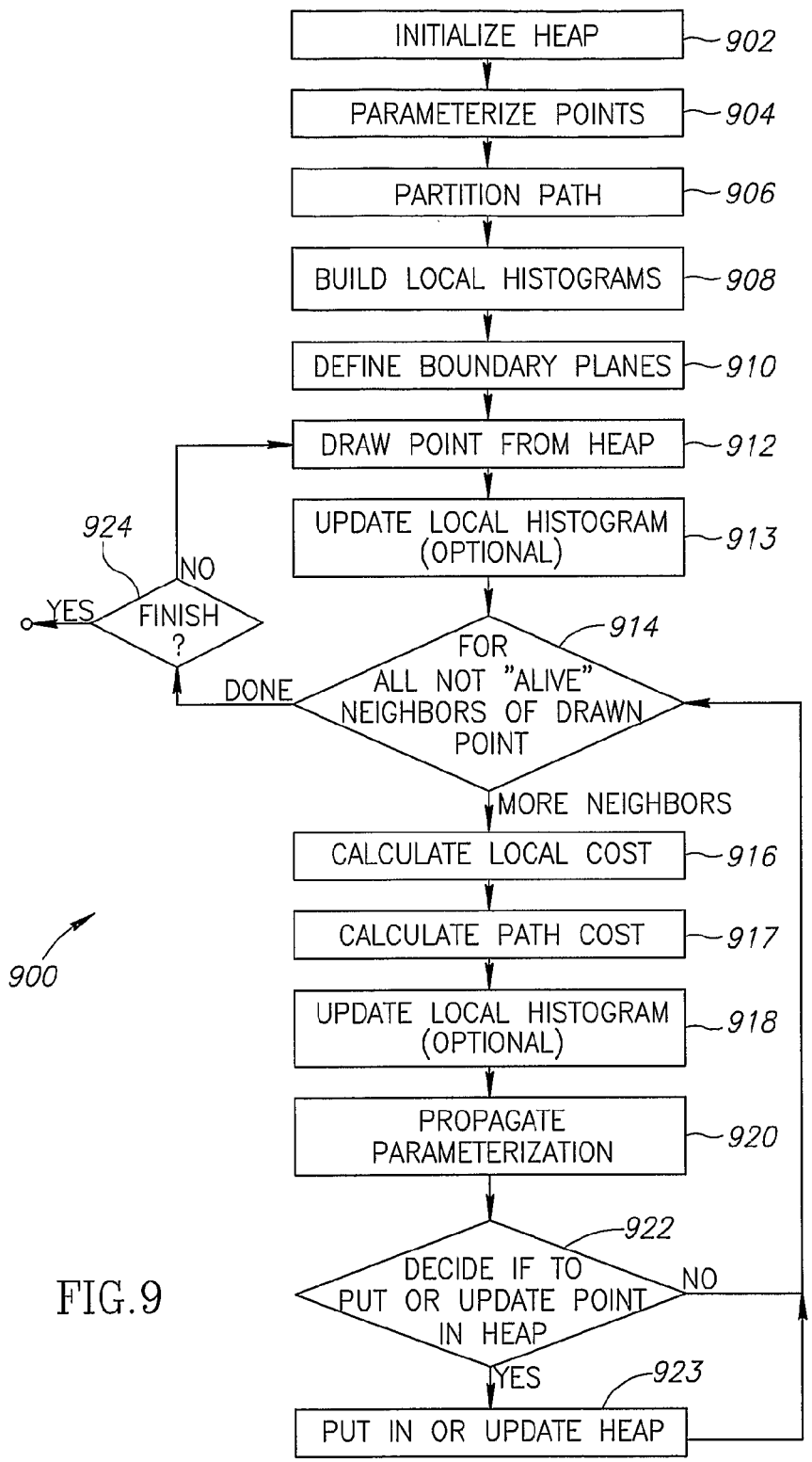
FIG. 9 is a flowchart of a method of segmentation based on an initial path, in accordance with an exemplary embodiment of the invention.

In the following description, a method of finding a centerline in a blood vessel is described, in which, FIGS. 2-6 illustrate various states during the application of the method, FIG. 7 is a general flowchart of the method and FIGS. 8-9 are more detailed flowcharts of particular portions of the method.

FIG. 7 shows a high-level flowchart 700 for an exemplary embodiment of the invention. At 702, a user enters data points indicating a path of the vessel. At 704, a path inside the blood vessel is found, connecting the points. At 706, the path, if not found as a single line, is optionally corrected. In an alternative embodiment, this is done at the end of the process (after 714), with some or more of acts 708-714 being performed on partial paths. At 708 the blood vessel volume is detected (segmentation). At 710, the segmentation is optionally improved. At 712, a map of the distances inside the blood vessel (from the vessel walls) is determined. At 714, a centerline is found from the distance map.

Data Entry

Figure 1:
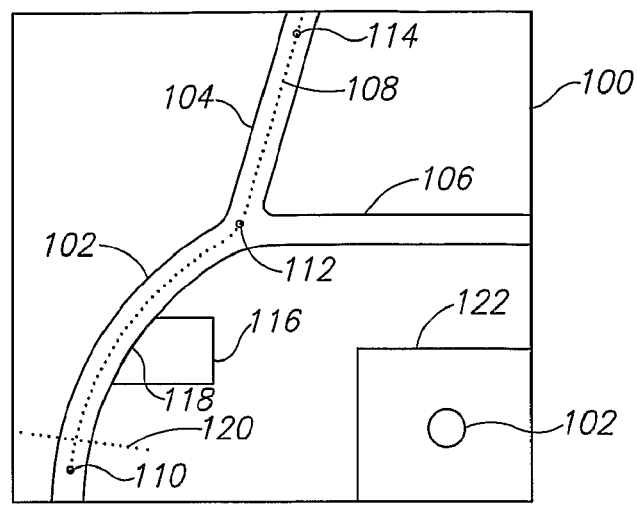
FIG. 1 is a schematic illustration of a display showing two blood vessel views.

Referring back to FIG. 1, a user enters a plurality of points to indicate the blood vessel of interest to the system. It should be noted that in some embodiments, the system will generate a centerline for all blood vessels or will automatically detect the blood vessel of interest (e.g., based on a constriction therein or based on a desired diagnosis) so that no user entry is required in such embodiments.

In a particular implementation, a user can mark points on one or more of a 3D view, and/or one or more slices or projections. Optionally, a windowing function is used to select only CT values in a range of possible blood vessel values, thus simplifying the image data set and allowing projection of relevant anatomical structures. Optionally, the data entry is performed on a digital image viewing station.

In the example shown, a user marks a starting point 110 and an ending point 114. A middle point 112 is optionally provided at a fork. While only three points are shown, more points, for example, 4, 6, 10 or more may be used. However, it is a property of some embodiments of the invention that only a small number of points is required for entry by a user, for example, fewer than 10, fewer than 8 or fewer than 5, or even 2.

While the method described below focuses on a single vessel (e.g., 102), optionally, the user can mark a bifurcation, for example, by providing a point in a bifurcation vessel 104 and a point in a bifurcation vessel 106. The method can show a forked centerline. Optionally, the method is applied twice, once for each bifurcation. Optionally, a user indicates when the points belong to bifurcations, rather than a convoluted vessel.

Once the method is executed, a centerline 108 is generated. Various known imaging methods may then be used, for example, methods of slices along the centerline, methods of slices perpendicular to the centerline and methods virtual endoscopy using the centerline as a path and/or viewpoint.

Optionally, the centerline is not restricted to pass through any of the user entered points. Alternatively, it may be restricted to some of the points, for example the starting and ending points and/or points indicated by the user as crucial. In some embodiments of the invention it is desirable to receive the user input for where the blood vessel is, but not force the user to be very precise in marking points along the exact centerline, which might be time consuming and/or difficult.

Initial Path Finding

Figure 2:
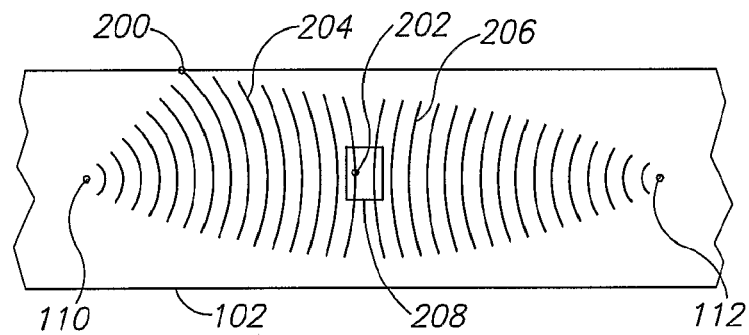
FIG. 2 is a schematic illustration of a blood vessel showing a stage of a path finding method in accordance with an exemplary embodiment of the invention.

FIG. 8 is a flowchart 800 of a method of finding an initial path in vessel 102, in accordance with an exemplary embodiment of the invention. FIG. 2 illustrates a stage during such path determination. For clarity in this and other figures, only user points 110 and 112 are shown. In general, this path finding method propagates a contour 204 from point 110 until it meets (e.g., at a point 202) a contour 206 propagated from point 112 (or point 112 itself). This propagation is optionally carried out under a restriction which attempts to reduce the chance of a point 200 along such a contour from leaving the boundaries of blood vessel 102. Another optional restriction is that the path be attempted to have a low cost (e.g., stay near center and/or be relatively short).

A targeted marching algorithm forms the basis of the method of FIG. 8, in accordance with an exemplary embodiment of the invention. In this algorithm, a plurality of points are stored in a heap, each with an associated total cost, and marked as "trial". At each step, a point with lowest associated total cost is removed from the heap, marked as "alive" and propagated to all its neighbors, for example its 6 nearest (Cartesian) neighbors. For each neighbor a total cost function combining path cost and expected cost to a target are calculated and then the neighbor is put in the heap. The path cost of a point is calculated from its local cost, and the path costs of its neighbors. This step is optionally repeated until all the points in the heap are used or the target reached. In the method of FIG. 8, meeting of points is tracked and if points from two source (user entered) points meet, then those points are deemed connected. Points that have not been visited yet are marked "far". The different types of marked points ("trial", "alive" and "far") may be processed differently. In an exemplary embodiment of the invention, a targeted marching method as described in a PCT application entitled "Targeted Marching", having attorney's docket number 032/04082, being filed on an even date in the Israel Receiving Office, the disclosure of which is incorporated herein by reference, is used.

Referring to FIG. 8, at 802, a heap is initialized and the user points (e.g., 110, 112, and 114) are put in the heap, each with its own unique label and an associated total cost of 0. The labels are optionally used for finding a starting user point for each point 202, as will be described below. Optionally, the user points are ordered geometrically or assumed to be so ordered. The user points are marked as "trial" and all the other points in the data set are marked as "far".

At 804 (which may be performed out of order), two user histograms are initialized. As will be described below, these histograms help decide if a point under consideration is probably inside or outside of a blood vessel. If a different method is used for such determination or if no such determination is made, fewer or more histograms may be used, possibly even no histograms. In an exemplary embodiment of the invention, the two histograms used are:

(a) an "outside" histogram showing the distribution of CT values for the whole data set; and (b) an "inside" histogram showing the distribution of CT values for points assumed to be inside the blood vessel.

In an exemplary embodiment of the invention, the user points are used to initialize the "inside" histogram. Optionally the neighbors of these points are entered as well, or other points with a high probability of being inside the blood vessel. It should be noted that in this implementation the inclusion of "in" points in the "outside" histogram is ignored, but it need not be.

Optionally, one or both histograms are binned, for example to ranges of 5 or 30 CT numbers. Alternatively or additionally, each gray value added to a histogram is added as a swath of 30 values.

In the description the term histogram has been used to stand for various methods of tracking data value distributions. However, it is not necessary to store a histogram. For example, a data vector may be used. Alternatively, a curve which approximates the distribution may be used. In another example, a neural network is used. Further, other methods of determining likelihood may be used, for example, as is known in the art.

In an exemplary embodiment of the invention, predetermining histograms, rather than dynamic histograms are used, in this and/or other steps are used. In another exemplary embodiment a function mapping CT values to a range (e.g., [0 . . . 1]), is provided.

At 806, a point with a lowest associated cost is drawn from the heap. If it is not a user point (or even if it is) (e.g., 807) it is used to update the "inside" histogram", by adding the point's gray value as a valid blood vessel value. Optionally, this allows points that are determined to be outside the blood vessel (e.g., high cost) to be left out of the histogram. Alternatively, the "inside" histogram may be updated as an unlabeled point is reached. In one such implementation, a value is entered into the "inside" histogram with a weight indicative of the probability that that value is actually inside. For example, a value is entered with a weight based on the cost function (the probability of being outside the blood vessel) described below. Alternatively or additionally, for the first 100 (or other number) points (e.g., voxels) encountered, the neighboring 50 gray levels are entered for each point, with a weight that decreases as a function of the number of points encountered so far (e.g., a linear reduction from $100/100$ to $1/100$). These and/or other methods may be used to bias the histogram so that gray values that are outside the histogram are prevented from taking over the histogram. If additional data (e.g., based on the medical procedure or expected diagnosis) regarding what values are expected inside or outside blood vessels is available, it may be used to bias the histogram (optionally at 804 and/or 807). Alternatively, it may be applied during the cost calculation described below. Optionally, 807 is performed only for some of the points, for example, for only the first 100 points.

Generally, a drawn point is marked as "alive" and will not be returned to the heap. However, in other implementations, such a point may be returned, for example based on finding a lower cost path (and/or estimate) thereto. Optionally, marked points are not returned to the heap if an estimation from below of the cost to target is provided and/or if a smooth estimation function is used.

At 808, the neighbors of the point are identified. It should be noted that the data set being used can be a 3D data set of cubic voxels. Each point thus has 26 potential neighbors. In an exemplary embodiment of the invention, only the six Cartesian neighbors are considered. As is known in the art of computing, the neighbors may all be determined at once, or one by one, for example as a previous neighbor is process, or even in parallel. For other representations (e.g., eight sided voxels), a different number of neighbors may be considered. In addition, also for cubic voxels, a different number of neighbors, for example, fewer or greater than six, may be considered.

For each such considered neighbor, references 810-828 are applied, and then a next point is drawn from the heap (806 again). A stopping condition may be applied, for example at a reference 830, as will be described in more detail below.

Referring to FIG. 2, the point drawn from the heap can be, for example point 202 and its neighbors be indicated by a reference line 208.

At 810, a check is made to see if the neighboring point is "alive", "far" or "trail". If it is "alive", a check (812) whether it has the same label as point 202. If it has the same label (814), the neighbor point is ignored.

If the neighbor point did not have the same label as point 202, a note is made that a connection between two user points was made (816). Once a user point is connected on either side to other user points (or, if an end point, on only one side), propagation from that point is optionally stopped. Once all user points are connected, the process can be stopped (e.g., at 830). In either case, a substantial reduction in the task is optionally achieved (818).

If the neighbor point is "far", it is labeled (at 820) with the label of point 202, and marked as "trial". In some implementations, a same flag is used both for the label and for the marking of a point and "far", "alive" or "trial". In some implementations, it is the presence in the heap that marks a point as "trial" and the distinction between "alive" and "far" is whether or not the point has a label. Optionally, a trial point is labeled and a copy of its old label saved. If it is decided not to update the point (e.g., at 828), the old label may be restored.

At 822, a local cost of the neighbor point is calculated, for example, using the formula cost=p(value|out)/(p(value|in)+p (value|out)), where p(value|in) answers the question "what is the chance of seeing this value given that we are inside of the vessel". The p( ) function is optionally based on the "inside" and "outside "histograms". This is a private case of Baysian probability calculation in which the weighing is even for being inside or outside. In some embodiments, non-even weighting is sued. Optionally, prior knowledge about the data set may be used to skew the weighting or to change the p( ) functions. This local cost indicates the likelihood of the point being outside the blood vessel.

It should be noted that point 200, for example, being at the boundary of the blood vessel will probably have neighbors with very high costs (e.g., as they are outside the blood vessel) and thus they will probably not be drawn. Also, it may be expected in some situations that as a point is closer to the wall of the blood vessel it will be more likely to have a value associated with being outside the blood vessel. However, this is not always correct (e.g., due to non-uniform mixing of a contrast material).

In an exemplary embodiment of the invention, the resulting local cost for the neighbor point is a weighted average of the cost formula for points in its vicinity. In an exemplary embodiment of the invention, the cost formula is applied to all 26 nearest neighbors (if they exist) and to the point itself and averaged using a weighing as follows: 4 for center point, 3 for Cartesian neighbors, 2 for semi-diagonal and 1 for diagonals. Then the result is normalized to the range 0 . . . 1 (e.g., by dividing by 54). In alternative embodiments of the invention, fewer or more immediate (or less immediate) neighbors may be averaged.

At 823, the local cost is used to calculate a path cost. In an exemplary embodiment of the invention, the method used in fast marching is used also for targeted marching. In one example, the following equation is solved for u, a searched for path cost:

$$P^2 = \max(u - U_{x-1,y,z}, u - U_{x+1,y,z}, 0)^2 + \max(u - U_{x,y-1,z}, u - U_{x,y+1,z}, 0)^2 + \max(u - U_{x,y,z-1}, u - U_{x,y,z+1}, 0)^2$$

where P is the local cost and U are the path costs for each of the points that are Cartesian neighbors for which cost is being calculated. In some cases a solution is not possible. A best fit may be searched for. Alternatively, one or more of the "max" units may be replaced by zero. In an exemplary embodiment of the invention, a "max" unit to be replaced by zero is selected in the following manner. For each "max" unit, the smaller U value is found. Then, the "max" unit for which the smaller U value is largest, is selected for removal.

Points which are not "alive" or points whose label is different than that of the neighbor, are optionally assumed to have infinite cost. While the description suggests storing the total cost, a path cost may also be stored for each point. Alternatively, the path cost may be extracted from the total cost.

In an exemplary embodiment of the invention, 823 acts as an interpolation of the path cost at a point using the path costs of the neighbors and the local cost at the point. Alternatively to the formula shown, a different interpolation may be used, for example, an interpolation that is skewed in one direction (taking for example information from left points into greater consideration than points on the right). In addition, the interpolation may be of a greater order and/or using a larger neighborhood, such as two neighbors away.

At 824, a target point for the user points is selected, for which to calculate the estimated future cost. In some cases a target is available on only one side and a nearest one is selected. In an exemplary embodiment of the invention, the following method is used to select between two points. A vector v connecting the neighbor point and the user point of the same label (e.g. the user point it started from) is projected onto two normalized vectors t1 and t2 which connect the starting point with the candidate target points. The point whose vector has the larger projection, is selected as a target point. This can be calculated by finding which of <v,t1> and <v,t2> is larger (where <,> denotes a scalar multiplication of vectors).

At 826, a cost to the target is estimated. In an exemplary embodiment of the invention, the estimate is based on the distance to the target and the average cost per unit distance so far. In one implementation, the average unit cost is the path cost to the neighbor point divided by the distance from the starting user point to the neighbor point, which is in turn optionally estimated by the Euclidian distance between the points. Then, the estimation of the future cost is optionally generated by multiplying the average unit cost by the geometrical distance to the target point.

At 828, the path cost and the estimated cost are added together to give a total cost, which is associated with the point and added with the point to the heap. For neighbor points which are trial points (e.g., in the heap), the associated path cost is updated (if lower), as the point does not need to be added.

Optionally, the total cost of a point is normalized to the distance between the starting user point and the target user point.

It should be noted that several types of costs are provided in some embodiments of the invention:
 a) Path cost—the cost to reach a point.
 b) Local cost—the cost added by particular properties of the point, for example CT number.
 c) Estimated cost—the cost estimated for reaching a target point.
 d) (Normalized) total cost—the sum of path cost and estimated cost, optionally normalized and associated with each point.

At 830, various stopping conditions may be tested. For example, if the lowest cost point in the heap is too high or if too much time has passed the path finding method may be stopped. In an exemplary embodiment of the invention, a budget of points to be visited is provided for various stages of the method, for example, 2,000,000 points each for path finding and segmentation.

Figure 3:
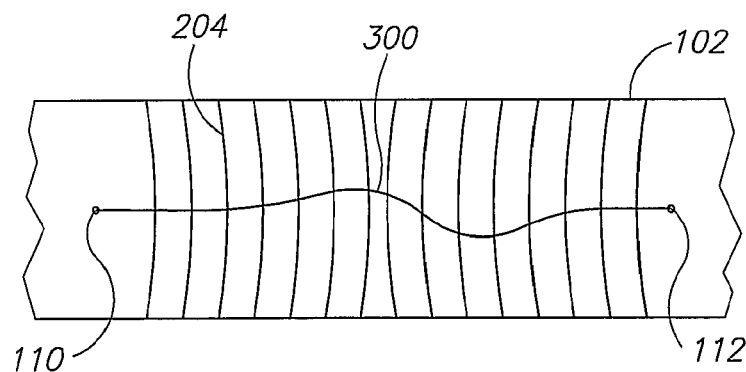
FIG. 3 is a schematic illustration of a blood vessel showing a further stage of a path finding method in accordance with an exemplary embodiment of the invention.

At 832, the initial path is generated. FIG. 3 shows a vessel segment in which a plurality of contours 204 were propagated and showing an initial path 300 connecting user points 10 and 112. This line may be found, for example, by connecting together all the meeting locations between different labeled points using, for example, (generally less preferably) straight lines or lines that travel along the lowest cost path (e.g., using gradient descent or other methods). In an exemplary embodiment of the invention, this path is found by advancing the path always to the neighbor with the lowest cost.

It should be noted that many path finding methods may be used instead of the method of flowchart 800. In an exemplary embodiment of the invention, however, a method is chosen in which any such path remains inside the blood vessel volume. Desirably, for reducing processing costs and/or preventing the determination of bad paths, the search is also focused to remain inside the blood vessel.

Path Correction

At 706 (FIG. 7), the found initial path may (optionally) be corrected. In one instance, a user may desire to correct the path. In another instance, a full path may have not been found (e.g., due to a time limit or the existence of an occlusion in the blood vessel). In an exemplary embodiment of the invention, a user can connect between found partial paths.

In an exemplary embodiment of the invention, partial paths are connected by applying the targeted marching method with a local cost of 1. This will tend to connect segments with straight lines. The points to be attached, can be, for example user points, or points on the contours extended from user points Alternatively or additionally, the targeted marching method may be reapplied for sections where a path was not found, using relaxed constraints, for example, accepting more gray values as possibly being part of blood vessels.

Alternatively, a plurality of partial paths resulting from the method of FIG. 8, are passed on to the following stages and the final generated centerline is composed by linking together centerlines generated for each segmentation corresponding to a partial path.

In other embodiments, no path correction is performed.

In an alternative embodiment of the invention, an initial path is provided by a user. In one example, the paths are drawn in a free hand manner. Optionally such a user provided path is corrected, for example, by removing sections of the path that clearly cross vessel boundaries (e.g., based on grey levels). These sections may be connected, for example, using a line within the vessel Segmentation Once an initial path 300 is found, segmentation (708) is used to select which part of the data set is the blood vessel of interest. In effect, this selection defines a segment that is the blood vessel (or a section thereof between the user points 110 and 114).

Figure 4:
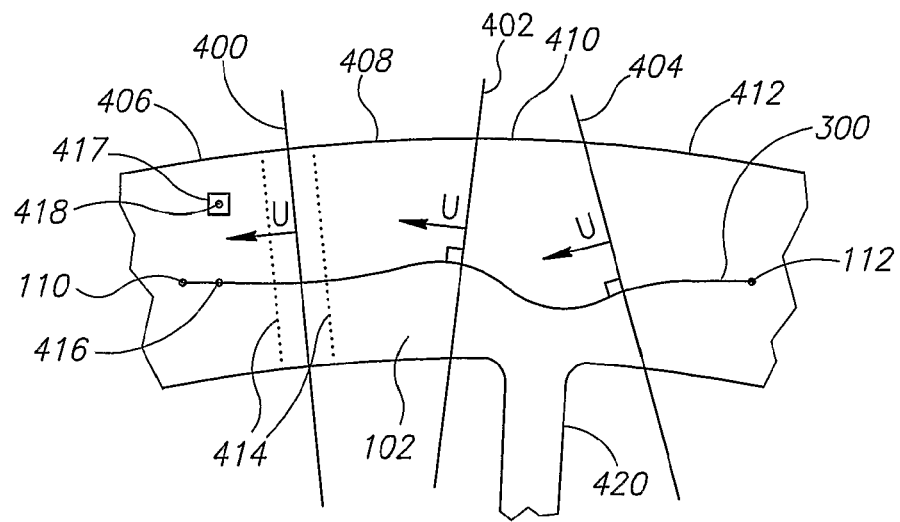
FIG. 4 is a schematic illustration of a blood vessel showing a stage of segmentation, in accordance with an exemplary embodiment of the invention.

FIG. 4 shows a section of blood vessel 102, shown radially curved, for clarity, during such segmentation. FIG. 9 is a flowchart 900 of a method of segmentation based on initial path 300, in accordance with an exemplary embodiment of the invention. In an exemplary embodiment of the invention, this method expands initial path 300 to fill the blood vessel volume. Flowchart 900 is of a method based on a "fast marching" method, for example as described in Laurent D. Cohen, R. Kimmel, "Global Minimum for Active Contour Models: A Minimal Path approach", in International Journal of Computer Vision 24(1) (1997), 57-78 and in J. A. Sethian, "Level Set and Fast Marching Methods", Cambridge university press (1996), the disclosures of which is incorporated herein by reference. However, other methods can be used as well, for example morphological methods and expansion of centerline methods. In addition, in an exemplary embodiment of the invention, various methods to prevent or reduce "leaking" from the blood vessel are optionally practiced, for example as described below. It should be noted that the fast marching method does not include target selection and target cost estimation, but may use a same type of conversion form local cost to path cost.

At 902, the heap for the fast marching method is initialized, with all of the points along path 300, optionally, with their immediate neighbors, all with a cost of 0.

At 904, each point is optionally associated with a value of a parameterization. This may be used to prevent leaking and/or to ensure correct direction of propagation, as described below. In an exemplary embodiment of the invention, the parameter is an integer ordinal number starting at 1 for point 110.

At 906, the blood vessel/initial path is partitioned into a plurality of portions (shown as 406, 408, 410 and 412). In an exemplary embodiment of the invention, each portion is made 50 points wide along path 300. Optionally, the size of the segments is a parameter which may be related, for example to the expected vessel diameter or to the curvature of the curve. Optionally, the size of the segments is selected to optimize run time and/or prevent escape. Optionally, the selection is by executing the algorithm on a plurality of curvatures and/or vessel diameters.

At 908, a local "inside" histogram is built for each portion 406-412. Optionally, the local histograms are smoothed and/or shared between nearby portions, for example, a same local histogram may be shared between three segments. Optionally, the histograms are binned. Alternatively, each gray value of path 300 is inserted together with values 20 higher and 20 lower (or some other range). Alternatively, no local histogram is used, for example, reusing the "inside" histogram of FIG. 8 or not using a histogram at all.

In an exemplary embodiment of the invention, a global "in" histogram is constructed and used as a filter such that only points with a high likelihood in the global histogram are entered in the local histogram. Optionally, this helps avoid outliers, and prevent occlusions from overwhelming a local histogram. Optionally, the global "in" histogram is not used after that.

Optionally, a same "outside" histogram as used in the path finding sub-process is used, optionally disregarding the inclusion of "inside" points in the histogram. A global or a local "outside" histogram may be used. In an exemplary embodiment of the invention, the inclusion of the "in" points makes building the "out" histogram simpler, as it can be done once at the beginning by a single pass over the data set, and does not require update as more information of the actual vessel is gathered. In order to do that it is optionally assumed that the volume of interest is fairly small compared to the size of the entire data set. In other applications, for example, where the vessel size is significant compared to the entire data set, whenever the "in" histograms are updated, the "out" histogram(s) are also optionally updated.

At 910, a plurality of boundary planes 400, 402 and 404, which separate the portions, are defined. In an exemplary embodiment of the invention, these planes are generally perpendicular to the path 300, and as a result somewhat perpendicular to the vessel walls, however, that is not guaranteed. In an exemplary embodiment of the invention, the following definition is used. Vi is a vector that connects the two ends of a path section (normalized). Ui, is a vector that defines the boundary plane between a portion i and a portion i+1, and is an average of Vi and Vi+1. The boundary planes are perpendicular to Ui. Ui are optionally normalized.

At 912, a point (e.g., a point 417) with a lowest associated cost is drawn from the heap. Optionally, each portion has a separate heap, but this is not required.

At 914 rubrics 916-923 are applied to the neighbors of the drawn point. Optionally, only the six Cartesian (nearest) neighbors are considered. In an exemplary embodiment of the invention, "alive" neighbor points are ignored, while "trial" neighbor points are allowed to have their cost updated in the heap.

For clarity, a neighbor point 418 is discussed below.

At 916, a local cost for point 418 is calculated (described in greater detail below).

At 917, a path cost is optionally calculated (described in greater detail below).

At 918, the value of point 418 is optionally used to update the local histogram. The methods described above are optionally used, with a smaller cut-off (e.g., special treatment for the first 20 points). Alternatively, the histograms need not be updated, just being based on the original path 300 and its neighbors (e.g., nearest 6 or 26 for different embodiments). Optionally, the updating is performed between 912 and 914. Optionally, the drawn point, rather than point 418 is used for the updating. Optionally, 918 is carried out as 913, with the drawn point being used, rather than point 418. Optionally, any given point is only used once for histogram updating.

At 920, a parameterization value is associated with point 418.

At 922 a decision is made if to put point 418 into the heap or not.

At 923, a point may be added to the heap or its cost updated, if so decided at 922.

Rubrics 912-923 are repeated. Optionally, a stopping decision 924 may be applied. One example stopping decision is to stop if too many steps were performed (e.g., too many points considered). Another example is a time limit. Another example is if the heap is empty. Optionally, the stopping conditions are applied separately for different path portions.

Referring back to 916, the local cost function optionally includes a logic portion and a calculated portion. The calculated portion decides a value for the cost and the logic portion decides if to give a binary cost value (e.g., 0 or infinite). Optionally, these values are interpreted as "0" meaning the point is in a vessel and infinite meaning probably not and optionally reconsider. In an exemplary embodiment of the invention, the local cost function is as follows:

(a) Determine the path portion point 418 belongs to, for example, based on its parameterization value, the parameterization value of the point it originated from and/or based on the parameterization of the point drawn from the heap (e.g. 417). In an exemplary embodiment of the invention, for example if the parameterization of point 418 is not yet determined, the path portion is determined by looking at the parameterization of the point that was drawn from the heap.

(b) Collect and count the number of nearby points that are semi-diagonal to it. These points are neighbors that share exactly one of an X, Y and Z plane used to locate point 418 in space. Optionally, the local cost is a combination of 2 values that are calculated based on the collected points: P and AD, where P is an indicator of the likelihood of the CT values of the points, and AD is an estimation of the curvature at 418.

(c) Pav is the average value cost (e.g., calculated using the formula cost=p(value|out)/(p(value|in)+p(value|out)), optionally for the semi-diagonals, based on the local histogram of the path portion) for each of the collected points. P is optionally defined as a weighted average of the value cost Pvc (20%) and Pav (80%). Pvc is the value cost of 418 based on the same formula as Pav. P is used to hold the intermediate cost for point 418, which is used to calculate the local cost that is the final result of 916.

(d) If AD, the number of collected points that are "alive" (e.g., already processed) is smaller than 2, the local cost for point 418 is infinite. Optionally, this prevents leakage and/or smoothes the resulting segmentation.

(e) If AD is greater than 6, then the local cost for point 418 is 0. Optionally this fills cavities and smoothes the segmentation.

(f) If the intermediate cost P is greater than 0.6, then the local cost is infinite. Optionally, this helps avoid leakage from the blood vessel. Optionally, different thresholds are used for different situations, for example, for images of the neck, a threshold of 0.9 is used and, optionally, if Pvc is greater than 0.9 (or 0.6 for other embodiments) the local cost is made infinite.

(g) Otherwise, the local cost is a function of P and AD, that increases with P and decreases with AD.

It should be noted that this particular cost function generally prevents propagation with high curvature, as increased AD is associated with small local curvature. This means that segmentation method prefers filling cavities over generating spikes. Optionally, different neighbors are differently counted for the purpose of estimating curvature. In one example, nearer neighbors are counted with a greater weight. In another example, neighbors closer to a boundary are counted differently from neighbors closer to a centerline. In another example, what is counted is a distribution of the visited points, for example, requiring (e.g., for a certain curvature value) that visiting points be evenly or unevenly distributed spatially.

Other methods of estimating curvature may be used as well. For example, curvature can be estimated from the second derivatives of the actual image data (e.g., rather than merely counting neighbors). In another example, curvature can be calculated by interpolation of the path cost values (e.g., rather than just checking how many of the cost values are not infinite).

At 917, a path cost is calculated from a local cost, for example using a fast marching method, for example, as described above in 823.

Referring back to 920, a parameter value for point 418 is calculated. In an exemplary embodiment of the invention, the new value is selected so that the gradient of parameterization of the points in general is generally parallel to the gradient of parameterization of path 300. In an exemplary embodiment of the invention, this is achieved by selecting a value such that the scalar multiplication of a parameterization gradient and a path cost gradient is zero. Both gradients are optionally interpolated or extrapolated from the points used to calculate the local cost (e.g., the AD points). Alternatively, a different set of vicinity points is used, for example, the six nearest neighbors or all the immediate neighbors.

Referring back to 922; a decision not to put a point in the heap is optionally based on one or more of the following conditions:

(a) If the cost is infinite or above some predefined threshold.

(b) If point 418 goes beyond the planes at the path portion ends. Optionally, a safe zone (e.g., 414) is defined within which points from one path portion can encroach on another path portion. In an exemplary embodiment of the invention, the origin portion of point 418 is determined from its parameterization value. In an exemplary embodiment of the invention, the encroachment is determined as follows. A vector connecting point 418 to each of the ends of the portion is projected on each of the plane normal vectors U of these ends. If the projections are positive (or above a threshold, for example −20, to accommodate zone 414), then point 418 is within its allowed portion. It should be noted that for a point between 400 and 402 the connecting vectors are actually (1) the vector connecting the part end at 402 with the point, and (2) The vector connecting the point to the end at 400. Optionally, this is used to ensure both vectors point forward so that the projections are positive.

(c) If point 418 strays too far from path 300. This may serve to prevent leakage or travel into side branches of blood vessel 300, for example a side branch 420. In general, it is assumed that the width of the blood vessel changes gradually. Thus, any sharp changes in the profile indicate a leakage or excursion into a side vessel. While this (sharp changes) may be dealt with during post processing, in an exemplary embodiment of the invention, it is dealt with as part of the segmentation. In an exemplary embodiment of the invention, one or both of limiting a radius and limiting a volume associated with a point, are used to prevent or reduce leakage.

In an exemplary embodiment of the invention, a count is maintained of the number of points with each parameterization value (that is points with the same integer portion of a parameterization value). Roughly, the count can be equal to the volume propagated from an original point. Any points with a count that is 150% of an average count avcount, are optionally discarded. Any points with a count between 100% and 150% are penalized by multiplying their local cost by $(count/(1+avcount))^2$. Optionally, this penalization prevents leakage by regularizing the volume that is gained along the vessel. Optionally, the average count avcount is made on the 9 parameter values greater and 9 parameter values smaller than that of point 418. Optionally, such processing is carried out depending on the availability of sufficient statistics for a point's parameterization (e.g., if the count of the parameterization is greater than 20).

Alternatively or additionally to limiting a volume of propagation, radius of propagation may be limited. It should be noted that depending on the location of the path relative to the lumen and depending on the uniformity of the lumen, one or the other of the limitation methods may be more accurate. Optionally, both methods are applied. Optionally, the methods are not applied so strictly as to prevent segmentation in most cases. Optionally, the speed of segmentation may be traded off with quality, by changing these or other limitation on propagation.

In an exemplary embodiment of the invention, radius of propagation is restricted by measuring or estimating a distance between the point and the path and preventing further propagation if the point is too far. Optionally, the above limits of 50% (etc.) change if an average of 18 neighboring points is applied. Alternatively or additionally, the limits may change over the neighbors may change as well.

Optionally, an accurate distance of point 418 is used. In one example, the actual distance of point 418 to the original point it came from (e.g., a path point 416 with the same integer part of a parameterization value as point 418). This distance is compared to the average maximum distances achieved by points of similar parameterization (e.g., the average is taken −9 to +9 in either direction of the parameterization value, or a different, symmetric or asymmetric neighborhood). Optionally, a table is maintained in which for each parameterization value (or a group thereof) a maximum distance achieved by points of that parameterization (integer part) value, is stored. Optionally, the table is used only if a point 418 has a distance above a minimum distance from its path origin point, for example, sqrt(10). Alternatively, the distance may be estimated, for example, using Manhattan distances.

Alternatively or additionally, for example when segmenting blood vessels in the neck, a similar method is applied to the path costs. Points with a path cost that is greater than 150% the average path cost of points with the same parameterization value (or an average of 9 points on either side) are rejected from the heap, and points between 100% and 150% are penalized. Optionally, this prevents leakage by regularizing the radius of the vessel.

(d) If point 418 was not propagated generally perpendicular to path 300. For example, if a line connecting points 416 and 418 is not generally perpendicular to the path at point 416, the point is discarded. Optionally, some leeway is allowed, for example, 10 or 20 degrees away from the perpendicular. Alternatively to using the path at 416, the line connecting point 110 and point 416 may be used as an approximation. Optionally, the limitation of perpendicular is used in neck cases. Optionally, this limitation is used to limit leakage.

In an exemplary embodiment of the invention, the propagation condition is estimated as being the angle between the vector connecting points 416 and 418 and the gradient of the path cost. If the angle is above than 45 degrees, the angle is considered to be too great.

In an exemplary embodiment of the invention, a rigid distance limitation which limits perpendicular propagation from the path is provided. This limitation may be, for example instead of or in addition to the dynamic volume and radius limitations described herein.

Optionally, a model of the vessel or organ may be provided and used as a propagation limitation in one example, the model is fixed (e.g., a cylinder). In another example the model is parametric (e.g., defining relative radii of different parts or allowed curvature as a function of relative length of the organ). In an exemplary embodiment of the invention, the distance from the model or from a model of the centerline is used to augment the local cost function.

In an exemplary embodiment of the invention, segmentation radial expansion is optionally limited by statistics, rather than, or in addition to, using parameterization. In one example, for each segment radius and distance statistics are maintained for each segment rather than for each point as in parameterization.

In an exemplary embodiment of the invention, parameterization is propagated using morphological methods. In one example, dilation is used so that new points/voxels get a parameter value of, for example, the parameter value of one of their neighbors, the mean value of parameter values of its neighbors or a majority value of parameter values of its neighbors.

The following features of flowchart 900 should be noted as being possibly useful in preventing leaks: avoidance of areas with improbable gray values; avoiding narrow paths by controlling local curvature; avoid undue propagation along the path using boundary plane; limiting sideways leakage by forcing smoothness and/or limiting the total number of propagation steps. Optionally (e.g., for neck images) an infinite cost value is provided for points with an unlikely gray value. For example, if the likelihood of being outside is over a threshold such as 90%, the cost is made infinite.

Other segmentation methods may be used as well. In one example, for every point in that found path a 2D plane through the point that is perpendicular to the path at that point is selected and a 2D segmentation is applied to that 2D plane. This 2D segmentation can use the methods described herein or known methods. These 2D segmentations can be added together to an approximate 3D volume. Any remaining holes in the volume may be repaired, for example by smoothing.

Clean Segmentation

Optionally, at 710, the segmentation is cleaned. In an exemplary embodiment of the invention, small leaks are corrected by removing all points that have two neighbors on opposing directions that are outside the segmentation. This is shown in FIG. 5, where a small leak 500 is removed using this method.

Distance Transform

Once the segmentation is found, a centerline may be determined using one or more of various methods. In an exemplary embodiment of the invention, the centerline is determined by first generating a map of the distances from the boundaries of the segmentation and then finding a path along the distances. Alternatively, other methods, such as morphological skeletonization or thinning are used.

In an exemplary embodiment of the invention, a fast marching method is used to associate with each point in the segmentation a distance from the outside of the segmentation. The fast marching method is applied with each point in the boundary of the segmentation being initially in the heap with a cost of 0 and the local cost function being 1 (e.g., a pure geometrical path cost calculation). Other methods may be used as alternatives, possibly inferior, to fast marching, for example, Dijkstra's method of breadth-first search. In an exemplary embodiment of the invention, points on the boundary of the segmentation are defined as any points with neighbors outside the segmentation. FIG. 6 shows a plurality of lines 600 each corresponding to an iso-cost set of points in the data set.

Centerline Finding

Referring to FIG. 6, various methods may be used to find a path 602 from point 110 to point 112. For example, a ridge following method may travel along the "ridge" of highest distance values found in 712, optionally with some smoothing.

In an exemplary embodiment of the invention, a targeted marching method is used, such as described above for initial path finding. In this implementation, only the two end points (110 and 112) are placed in the heap, with the target at any step being the end point from which the method did not start. While even a single point could be used, a potential advantage of using two points is that search time may be reduced.

While the local cost function can simply be the inverse of the distance value found in 712, in an exemplary embodiment of the invention, a more complex function is used, which may assist in providing a smooth centerline. Optionally, the correction is used for keeping the path in the center. Optionally, this function takes into account the diameter of the vessel, optionally enabling the method to tradeoff a desire to stay in a center of the blood vessel with a desire to reduce curvature.

In an exemplary embodiment of the invention, the following method is used to calculate the local cost function of a point P:

(a) p is set to be the parameterization value found in 708.

(b) MaxD(P) is an estimate of the diameter at point P, for example, the maximum distance achieved for any point with parameter p that has the same integer portion as the parameter of the point P. Optionally, MaxD is calculated and stored in the distance calculation stage.

(c) avMaxD(P) is an average on the neighbor parameters of p, for example, three higher and three lower.

(d) D(P) is the distance of point P, found in 712.

(e) cost=alpha*beta^(D(P)/avMaxD(P))+omega. Optionally, if avMaxD(P) is zero, D(P)/avMaxD(P) is set to zero or some other constant, to avoid division by zero.

(f) omega is a small value used for smoothing, generally close to zero. Alpha is a scaling term selected to adjust the other values (e.g., to match omega) and beta is a value reflecting a tradeoff between desiring a short path and desiring the path go in a middle of the blood vessel. Generally, shorter paths have a smaller curvature. Optionally, normalizing D(P) by avMax(P) makes the tradeoff of center vs. curvature more independent of the blood vessel diameter. In one example, omega is 0.001, alpha is 10,000 and beta is 0.00001. Optionally, omega is set to zero.

In some embodiments of the invention, a single path was not found in at 704, but rather a plurality of partial paths. Each such partial path is processed as described above and at the end, their centerlines 600 connected, for example, using straight lines. Optionally, smoothing is provided at the connection points. Optionally, such smoothing is applied to the attachment section, not to the calculated centerline.

Rather than targeted marching, other search methods can be used, for example, Fast Marching, Dijkstra or A*. These methods may be used, alternatively or additionally, for finding an initial path (704), and a centerline (714).

The above has been described for CT images. However, it may be applied to other modalities as well, albeit that such modalities may not be as problematic. In such modalities various of the parameters may need to be changed and/or optimized. For example, the degree of smearing in histogram values may be changed. Also, while 3D data sets are used, in some embodiments of the invention, 2D data sets of analyzed using the methods described herein.

The above method may be applied on vessels of various sizes, for example from 2 mm to 25 mm, for example with a voxel size of less than 1 mm or less than 0.7 mm or 0.5 mm. For example, a centerline may be found for the aorta, from its arch to the iliac arteries, for renal arteries, for vertebral arteries, for internal carotids.

In an exemplary embodiment of the invention, the method used above for trading off curvature has one or both of the following properties: (a) the tradeoff between line length (proportional to curvature) and staying in the center is relatively uniform in various radial distances, e.g., the tradeoff is the same when on the surface of the vessel, and when partly inside (e.g., 5% from surface to center), or significantly inside (e.g., 30% from the center). Another property is that (b) the tradeoff is uniform also in parts of the vessel that are of a different width, for example the tradeoff is the same when you are on the surface of a narrow vessel, or on the surface of a wide vessel, for example, within a factor of width of 1:2, 1:4 or 1:6. In some embodiments of the invention, property (a) is provided by the use of the exponent and property (b) is provided by the normalization of diameter.

While the method may be applied to voxel based methods, other representation methods can also be used with the vessel.

It should be appreciated that while a complete method of finding a centerline is described, in some exemplary embodiments of the invention, parts of the above method are used for other image processing task, possibly on other body parts and possibly on non-medical images. However, various of the above described features appear to be capable of providing a beneficial result for the task of centerline finding in blood vessels.

It should be noted that not all of the problems mentioned in the background can be guaranteed to be solved by all embodiments of the invention, instead, suspect situations may be provided to a physician to decide on, for example, indicating areas where a centerline could not be found. Alternatively or additionally, a physician can add points and/or change various parameters and ask the method to be executed again.

It should be noted that in some embodiments of the invention, not all of the user entered points are on the centerline. For example, possibly only the two end user points are used. Even these points are not required to be on the centerline, in some implementations. In an extreme case, a user can indicate one point in a blood vessel and allow the method to extend its search to the edge(s) of the volume. In another extreme case, all the blood vessels in a volume are centerlined, for example, based on an otherwise identified blood vessel.

In the above description many numbers are provided. In some implementations these numbers are parameters. In general, a user can optimize the values and/or other properties of the algorithm for particular cases, for example, particular types of CT images. In any case, these numbers should be considered examples of possible numbers and not absolutely limiting on the invention. In particular, some parameters may be changed for particular ranges of blood vessel diameters and/or types of problems. Also, when transferring to other problems, such as virtual endoscopy (or viewing of other lumens or solid elongate organs), other values may be useful.

A particular property of some embodiments of the invention is that only a relatively small number of points is required, and that other than requiring these points to be inside the vessel, they may be loosely placed (in some implementations, the two end points are held to higher standards).

In an exemplary embodiment of the invention, a blood vessel requires fewer than 2+3N points, where N is the number of occlusions and/or number of major stenosed areas in a blood vessel. In some cases, only 2+2N points are required. In others, 2+N points are sufficient.

It should be noted that various types of vicinities and neighborhoods were used above. In other implementations, the number of points in certain neighborhood may be increased or reduced. In one example, where heavy processing is required, fewer neighbors are considered. In another embodiment, for example for generating a line of travel or sight, either 6 or 26 neighbors are used, to prevent problems caused by semi-diagonals and their neighbors. It should also be noted that while averaging is widely practiced, it not required in every case, while it does usually provide a generally desired damping effect.

While the above methods have been described especially with reference to blood vessels, these methods may also be used for identifying and/or otherwise processing other ducts and tubular tissue in the body, even if they do not include lumens, for example, the urethra, the colon, the various ducts that are associated with the GI tract (e.g., pancreatic duct, bile duct, hepatic and cystic ducts), larynx, bronchi, trachea and nerves. In some cases, it may be beneficial to optimize the methods above for particular organs, for example, responsive to their diameter, thickness, branching behavior, specific tissue and/or nearby tissue X-Ray absorption and/or typical nearby tissue. Such optimization may result in faster execution, lower memory requirements and/or fewer errors.

In an exemplary embodiment of the invention, for the urethra, the optimizations suggested for the neck are used. Such optimizations may also be used for other narrow diameter vessels. Optionally, these optimizations are used for other narrow ducts of the GI tract, for example when enhanced with contrast material.

In an exemplary embodiment of the invention, for the colon, one or more of the following changes are optionally applied.

(a) Changing one or more of the bin sizes of the histograms, the number of voxels used to update the histograms (806) and/or the number of neighboring gray levels added to the histograms e.g., at 804, 806, 908, 913. Optionally, if the colon is filled with air, as air has constant and known Hounsfield values the histogram based cost can be replaced by a cost that is 1 for gray values greater than (e.g., −800), and 0 otherwise. This is an example of thresholding. In general, for this and other applications, a user can perform a calibration, for example, per patient type, image type, imaging parameters, image acquisition and/or reconstruction method, tissue type and/or imaging modality, to determine various parameter numbers which yield a suitable and/or faster result of the above described vessel finding algorithms. A search method, for example steepest descent or another search method (many are known in the art) can be used for finding an optimal, near optimal or acceptable parameter set.

(b) Changing one or more of the segment size and safe zone size (in segmentation), AD to P ratio in local cost (Segmentation). Optionally, this change is useful to compensate for the larger diameter of the colon and/or to make use of the availability of generally dominant grey values in the colon (so the danger of leakage during segmentation may be reduced).

(c) Thresholds (Segmentation)

(d) The smoothness/center of centerline tradeoff values (Centerline), (e) An additional step may be needed after the segmentation to add to the segmentation the adjacent excrement. Optionally, this step comprises following the segmentation with another segmentation step that is initialized with the boundary of the first segmentation, and using a global "in" histogram that is initialized with all the voxels on the boundary of gray values greater than 200. Additionally or alternatively all connected components that are adjacent to the first segmentation may be added to it if they have gray values above 200, for example using known morphological tools of image processing.

In an exemplary embodiment of the invention, for other air filled ducts such as the trachea the same variations that were described for the colon may be used.

In an exemplary embodiment of the invention, for other ducts such as the pancreatic duct, larynx, bronchi and/or trachea, the same changes may be used. For example, changes in modality and/or duct gray level contrast and values may benefit from adjustments to the histogram values and segmentation thresholds, as noted in (a) and (c). Changes of geometry such as having curly ducts may suggest adjustments to the parameters and tradeoffs, as noted in (b) (d).

Parameterization propagation as described herein may also be used for other types of data and/or objects. For example the propagation can be used to segment objects of any size or shape or for other uses. In a general manner, a tubular surface in 3D is a 2D manifold that may be parameterized using 2 parameters: r, q, where r goes from 1 to n along the tubular surface, and q goes from 0 to 2*PI—which is the angle along a circle cut of the tube. At any given point into which the parameterization is to be propagated, the method can be used twice, once for r and once for q. For example, for r the equation "<grad(r),grad(path_cost)>=0 is solved, and similarly for q. For q since q is not continuous at the part where 0 meets 2*PI care in calculating grad(q) is optionally taken. In one example, the value PI (modulus 2*PI) is subtracted from the values of q in a given neighborhood close to 0 or 2*PI (only for the purpose of calculating grad(q)), so that values near PI will result. PI is then added (modulus 2*PI). For higher dimensions more parameterization values may be used. Similarly, the initial parameterization values may be defined along a surface (e.g., of any shape) or a plurality of surfaces, rather than along a line as described hereinabove.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. It is noted that some of the above described embodiments may describe the best mode contemplated by the inventors and therefore include structure, acts or details of structures and acts that may not be essential to the invention and which are described as examples. Section headings are provided only for ease of reading and should not be construed as necessarily limiting the contents of a section to that section.

Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

While the application has been described as methods, it is meant to also encompass apparatus and means for carrying out the invention, for example, suitably programmed computers, servers and/or client computers, hardware, ASICs and/or computer readable media having suitable software thereon, for example, diskettes optical storage and computer RAM.

The invention claimed is:

1. A method of centerline determination for a tubular tissue in a digital medical image data set defined in a digital data space, comprising:
    receiving coordinates of at least one start point and one end point inside a tubular tissue volume of the digital data space;
    automatically determining a path between said points that remains inside said volume, comprising using targeted marching which uses a cost function incorporating both path cost and estimated future path cost;
    automatically segmenting said tubular tissue using said path; and
    automatically determining a centerline for said tubular tissue from said segmentation,
    wherein said receiving, said determining a path, said segmenting, and said determining a centerline are all performed on a same digital data space of said digital medical image data set.

2. A method according to claim 1, wherein said tubular tissue comprises a body lumen.

3. A method according to claim 1, wherein receiving comprises receiving at most 4 points from a human user.

4. A method according to claim 1, wherein receiving comprises receiving at most 2 points from a human user.

5. A method accord to claim 1, wherein determining a path comprises propagating a sub-path from each of at least two of said received points until the sub-paths meet.

6. A method accord to claim 1, wherein determining a path comprises propagating a sub-path from one of said received points until it meets another of the received points.

7. A method according to claim 1, wherein propagating a sub-path comprises selecting a point and selecting a neighbor of the selected point for further consideration responsive to said cost function.

8. A method according to claim 1, wherein a path cost of a point is a function of a local cost of a point and a path cost of at least one neighbor of the point.

9. A method according to claim 8, wherein a local cost of a point is a function of a probability of the point being inside or outside of the tubular tissue.

10. A method according to claim 8, wherein a path cost is determined by attempting to find at least an approximate solution to an equation including at least one extreme-type function that returns an extreme value of its operands.

11. A method according to claim 10, wherein if a solution is not found, at least one of said extreme-type functions is replaced by a constant value.

12. A method according to claim 11, said extreme-type function to replace is found by a min-max method.

13. A method according to claim 10, wherein said equation includes an approximation of a gradient of the path cost.

14. A method according to claim 9, wherein said probability is determined using a histogram of data point values.

15. A method according to claim 14, comprising updating the histogram when a point is determined to be inside or outside of the tubular tissue.

16. A method according to claim 14, comprising updating the histogram when a point is selected.

17. A method according to claim 16, wherein said histogram is updated with a weight corresponding to a probability of the point being inside the tubular tissue.

18. A method according to claim 14, comprising generating a local histogram for a part of said tubular tissue.

19. A method according to claim 14, wherein the histogram comprises an outside histogram for point values that are outside the tubular tissue.

20. A method according to claim 19, wherein the outside histogram includes also points inside the tubular tissue.

21. A method according to claim 14, wherein the histogram comprises an inside histogram for point values that are inside the tubular tissue.

22. A method according to claim 1, wherein a path cost of a point is a function of a probability of the point being inside or outside of the tubular tissue.

23. A method according to claim 1, comprising selecting a target to be used in an estimating of said future cost.

24. A method according to claim 23, wherein said estimating is an underestimating.

25. A method according to claim 23, wherein said estimating is based on an average cost per distance unit.

26. A method according to claim 23, wherein said estimating is based on an Euclidian distance to said target.

27. A method according to claim 23, wherein selecting a target comprises selecting from two or more possible targets.

28. A method according to claim 27, wherein selecting a target comprises projecting two vectors, one for each of two potential targets on a vector connecting a current point with a starting point of the current point and selecting a longer projection.

29. A method according to claim 23, wherein selecting a target comprises selecting one of said received points.

30. A method according to claim 1, comprising correcting said determined path.

31. A method according to claim 30, wherein correcting said path comprising interconnecting path segments.

32. A method according to claim 1, wherein said segmenting uses a marching method for segmentation.

33. A method according to claim 32, wherein said marching method assigns a value for each point in said tubular tissue.

34. A method according to claim 32, wherein said marching method is a fast marching method.

35. A method according to claim 1, wherein said segmenting uses a contour expansion method.

36. A method according to claim 1, wherein said segmenting comprises generating a parameterization for points along said path.

37. A method according to claim 36, comprising propagating said parameterization.

38. A method according to claim 37, wherein said propagated parameterization is used to prevent leakage of said segmentation.

39. A method according to claim 38, comprising collecting propagation statistics for different parameterization values.

40. A method according to claim 39, comprising limiting propagation of at least one parameterization value based on said statistics.

41. A method according to claim 40, wherein limiting comprises limiting propagation to be substantially locally uniform for nearby parameterizations.

42. A method according to claim 38, comprising determining a direction of propagation from a propagation of parameterization values.

43. A method according to claim 37, wherein said parameterization is propagated substantially parallel to said path.

44. A method according to claim 43, comprising propagating said parameterization to being substantially perpendicular to a path cost gradient associated with said propagation.

45. A method according to claim 37, comprising controlling a direction of propagation based on said parameterization.

46. A method according to claim 1, wherein said segmenting comprises partitioning said path into portions.

47. A method according to claim 46, comprising defining boundary planes between said portions.

48. A method according to claim 46, wherein said portions overlap by a substantially small amount.

49. A method according to claim 46, wherein said portions are substantially straight lines.

50. A method according to claim 46, wherein said partitioning is used to reduce leakage of said segmentation.

51. A method according to claim 1, wherein said segmenting comprises propagating from said path.

52. A method according to claim 51, wherein said propagating is limited to be substantially perpendicular to said path.

53. A method according to claim 51, wherein said propagating is limited to be substantially locally uniform in a radial direction.

54. A method according to claim 51, wherein said propagating depends on a local curvature.

55. A method according to claim 54, wherein said local curvature is estimated by counting visited neighbors.

56. A method according to claim 1, wherein said segmenting comprises segmenting using a histogram of data values to determine a probability of a point being inside the tubular tissue.

57. A method according to claim 56, wherein different parts along said path have different histograms.

58. A method according to claim 57, wherein said histograms are created to vary smoothly between said parts.

59. A method according to claim 57, wherein a noise level in at least one of said histograms is reduced using a global histogram.

60. A method according to claim 56, comprising repeatedly updating said histograms during said segmenting.

61. A method according to claim 1, comprising cleaning the segmentation.

62. A method according to claim 1, wherein determining a centerline comprises generating a distance map of said tubular tissue, of distances from an outer boundary of said tubular tissue, inwards.

63. A method according to claim 62, wherein generating a distance map comprises using morphological skeletonization on said segmentation.

64. A method according to claim 62, wherein generating a distance map comprises using fast marching on said segmentation.

65. A method according to claim 62, wherein determining a centerline comprises finding a path in said distance map.

66. A method according to claim 65, wherein finding a path for said centerline comprises targeted marching from at least one end of said segmentation.

67. A method according to claim 66, wherein said targeted marching for finding a path comprises taking a local curvature into account.

68. A method according to claim 1, wherein said data set is three dimensional.

69. A method of centerline determination for a tubular tissue in a digital medical image data set defined in a digital data space, comprising:
receiving at least one start point and one end point inside a tubular tissue volume;
automatically determining a path between said points that remains inside said volume, comprising determining using targeted marching which uses a cost function incorporating both path cost and estimated future path cost, wherein a path cost of a point is a function of a probability of the point being inside or outside of the tubular tissue;
automatically segmenting said tubular tissue using said path; and
automatically determining a centerline for said tubular tissue from said segmentation, wherein said receiving, said determining a path, said segmenting, and said determining a centerline are all performed on a same digital data space of said digital medical image data set.

* * * * *